United States Patent [19]
Wyatt et al.

[11] Patent Number: 4,693,602
[45] Date of Patent: Sep. 15, 1987

[54] METHOD AND APPARATUS FOR MEASURING THE LIGHT SCATTERING PROPERTIES OF SMALL PARTICLES

[75] Inventors: Philip J. Wyatt, Santa Barbara; Steven D. Phillips, Goleta, both of Calif.

[73] Assignee: Wyatt Technology Corporation, Santa Barbara, Calif.

[21] Appl. No.: 668,711

[22] Filed: Nov. 6, 1984

[51] Int. Cl.⁴ ............................................. G01N 15/02
[52] U.S. Cl. .................................... 356/336; 356/343; 250/227
[58] Field of Search ....................... 356/336, 343, 338; 250/227, 564–565

[56] References Cited

U.S. PATENT DOCUMENTS

| | | | |
|---|---|---|---|
| 3,476,482 | 12/1969 | Howard et al. | 250/227 |
| 3,999,062 | 12/1976 | Demsky et al. | 250/227 |
| 4,015,135 | 3/1977 | Tipton, Jr. | 356/336 |
| 4,548,500 | 10/1985 | Wyatt et al. | 356/343 |

OTHER PUBLICATIONS

"A Polarization-Modulated Light Scattering Instrument for Determining Liquid Aerosol Properties", Hunt et al, *Applied Physics*, 1975.
"Passive Remote Smoke Plume Opacity Sensing: A Technique", Lilenfeld et al, *Applied Optics*, vol. 20, #S, 1981.

Primary Examiner—R. A. Rosenberger
Assistant Examiner—Crystal D. Cooper
Attorney, Agent, or Firm—Philip J. Wyatt

[57] ABSTRACT

The measurement of the scattering properties of very small particles by electro-optical means generally requires the use of an intense, though highly spatially inhomogeneous, light source such as a laser. Many instruments require, therefore, that the intersection of the particle stream with the illumination source be precisely regulated so that the flux incident on the particle be known accurately. A method and apparatus are described by which means the absolute intensity of the light incident on the particle need not be known. A special structure and measurement process are described by which means small particles are differentiated from larger particles grazing the illumination beam.

27 Claims, 7 Drawing Figures

METHOD AND APPARATUS FOR MEASURING THE LIGHT SCATTERING PROPERTIES OF SMALL PARTICLES

This invention was made with Government support under Contract No. DAAK11-84-C-0020 awarded by the U.S. Army Armament, Munitions and Chemical Command. The Government has certain rights in this invention.

PRIOR RELATED PATENT

The present invention is directed to a method and apparatus of considerable utility in the characterization of small particles by measuring their light scattering properties. In particular, this invention permits the use of spatially inhomogeneous light beam sources such as produced by lasers to achieve these measurements.

Expressly incorporated by reference herein is the following co-pending Patent Application:
  U.S. patent application Ser. No. 390,980,
  Title: Process and Apparatus for Identifying or Characterizing Small Particles,
  Inventor: Philip J. Wyatt and Gregory M. Quist,
  Date of Filing: June 22, 1982.

DEFINITIONS

The term "light" shall means electromagnetic radiation.

The term "size parameter" shall mean $\rho$, where $\rho = 2\pi a/\lambda$ and a is the means particle radius and $\lambda$ is the wavelength of the incident electromagnetic radiation in the medium in which the particles are measured.

The term "very small particle" shall mean any particle whose size parameter is less than one.

The term "small particle" shall mean any particle whose size parameter is less than six.

The term "large particle" shall mean a particle whose size parameter is greater than six.

The term "beam" shall mean light propagating in a parallel or nearly parallel direction.

The term "beam diameter" of an incident light source, with a Gaussian intensity profile, such as a laser, shall refer to the diameter of the beam measured between the points at which the intensity has fallen to $1/e^2$ the intensity at the center of the beam.

The term "scattering efficiency" of a particle shall mean the ratio of its total scattering cross section to its geometrical cross section.

The term "forward scattering direction" shall mean all rays, i.e. directed line segments, propagating at an angle less than 90 degrees with respect to the direction of the incident beam.

The term "backward scattering direction" shall mean all rays, i.e. directed line segments, propagating at an angle greater than 90 degrees with respect to the direction of the incident beam.

The term "impact parameter" shall mean the distance of closest approach of the particle from the center of the light beam.

For plane polarized light, the plane perpendicular to the direction of the wave's electric field is called the V-plane and said plane polarized light is vertically polarized with respect to said perpendicular plane. The corresponding H-plane is perpendicular to the V-plane and contains the wave's incident electric field.

The particles that we will be discussing primarily throughout this specification are particles between 10 nm and 1000 nm and the illumination sources are usually lasers operating in the visible portion of the electromagnetic spectrum. As will be evident to those skilled in the art of light scattering techniques, this restriction is unnecessary and, indeed, our invention could equally well apply to particles of sizes outside of this range and lasers producing radiation that is not visible.

SUMMARY OF THE INVENTION

A particle passing through a laser beam scatters light as a spherical outgoing wave. When the particle's size parameter approaches zero, the ratio of the light scattered in the forward direction to light scattered in the backward direction approaches unity. At the same time, the scattering efficiency rapidly approaches zero. The power density of a typical laser beam falls rapidly from the center of the beam in a Gaussian manner with the $1/e^2$ diameter typically from 0.3 to 1.0 mm. Thus the total amount of light scattered by a particle depends not only on its size and composition but also on its impact parameter with respect to the beam center. The accurate characterization of the particle by means of the light it scatters depends critically, for virtually all applications, on being able to differentiate between scattering signatures of a very small particle and the corresponding signature of a larger particle whose impact parameter is too large to yield meaningful scattering data for the available detection system. The present invention allows this distinction by collecting light over a relatively large solid angle in the forward scattering direction and a similarly large solid angle in the backward scattering direction. By measuring the ratio of these two quantities and measuring the scattered intensities in a few other directions with respect to the direction of the incident light source, the distinction between small and large particles is established with a high degree of certainty.

BACKGROUND

Figure 1:
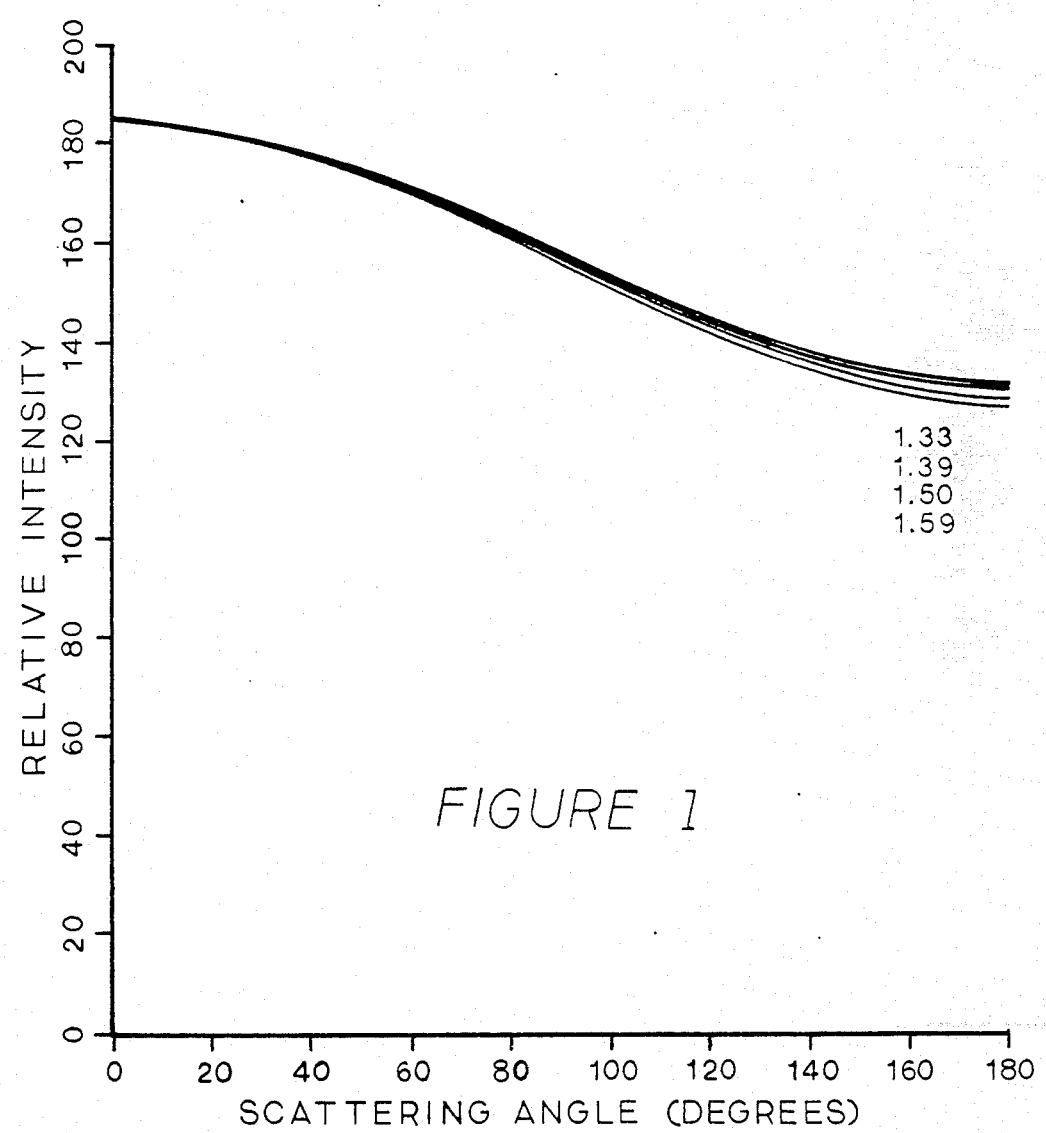
FIG. 1 presents the scattered intensity as a function of angle for spherical particles of several refractive indices and radius 50 nm.

The measurement and counting of aerosol and, to a lesser extent, hydrosol particles is an extremely important requirement for many types of industrial and health-oriented activities. Many critical manufacturing functions require the use of so-called clean rooms with the classification of such cleanliness based primarily upon the size and number of the largest particles present. In recent years, for example, the fabrication of very large scale integrated circuits, VLSI circuits, has required that the particle sizes present in areas where such devices are fabricated be less than 100 nm. The monitoring of work areas where asbestos insulation is being removed or where similar dangerous asbestos fibers are present requires, according to various Federal standards, that such fibers be monitored for both their presence and size. The performance of surgical procedures in operating rooms requires that the atmospheric environment be clear of particulates and especially bacteria. Indeed, even the manufacture and test of the high efficiency filters requires that they be checked by means of a particle sizing device. Many other types of biological and research endeavors could not be performed without the high efficiency filtering of the atmospheric environment and the continued monitoring of this environment for the presence of unwanted particles. There are other needs to monitor particles including the need to detect the presence of dangerous particles such as insecticides, bacteria, oxides of heavy metals, etc.

Because of the aforementioned requirements for the accurate classification and, especially, the sizing of very small particles, many types of instruments have been developed and marketed based on rapid electro-optical techniques. These systems generally require an illumination source such as collimated white light or a monochromatic light source such as a laser. Not only do lasers provide an exceptionally high light flux incident on particles passing through their beams, but they also play a major role in the spatial isolation of the particles because of their generally narrow beam cross section. A He-Cd laser, for example, as manufactured by Linconix, Inc., has a beam diameter of less than 0.3 mm.

Most traditional laser structures produce beams of the order of 1 mm. The term "beam diameter," of course, refers to the $1/e^2$ diameter, since the intensity profile of a $TEM_{oo}$ mode laser is Gaussian. This non-uniformity results in significant problems with "conventional" laser-based particle sizers since, for such instruments, the systems measure the total amount of light scattered by each single particle as it passes through the beam. The total amount of scattered light collected and measured is then associated with an average particle size. This assumption, that the total scattering cross section is proportional to the geometrical cross section, is erroneous, and is discussed, for example, in the article by Cooke and Kerker in Applied Optics, Vol. 13, page 272 (1974), or in Kerker's textbook *The Scattering of Light and Other Electromagnetic Radiation*. Nevertheless, all measurements of the deduced total scattering cross section, or any other relative scattering quantity, do require a knowledge of the intensity of the incident illumination. Obviously, the accurate placement of the particle precisely at the beam center is critical in the deduction of its "perceived" size.

The strip map technique, discussed in the corresponding patent application referenced above, does not require that each particle measured be exposed to an identical incident flux. Indeed, all subsequent characterizations (size, shape, refractive index, etc.) may be derived by considering various light scattering ratios or fractional differences between detected signals at different angular locations with respect to the direction of the incident illumination. Consider detector means distributed over the surface of a sphere with the light source illuminating a single particle at the center of the sphere. As long as each significant detector receives a sufficiently large scattered flux as the particle passes through the beam, the absolute position of the particle within the beam is not important. But if the particle to be analysed just grazes the beam, say at a $1/e^6$ distance, then the incident beam intensity on the particle may be too small to yield a meaningful signal at some detector locations. From the strip map input parameter requirements, such signals would result in meaningless values and, subsequently, erroneous particle classification. In order to establish that a larger (300 to 1000 nm) particle has grazed the beam and hence resulted in some measured intensities being significantly in error and that the particles, accordingly, cannot be classified, requires a new measurement technique. Very small particles (<300 nm), even if they strike the beam at its most intense region, will also scatter negligible light into most (or all) detectors. Thus, these particles too must be identified, distinguished from larger grazing particles, and classified, if possible. This invention describes a unique means to cope with the problems associated with the characterization of small particles, as well as the handling of larger, grazing particles.

DETAILS OF THE INVENTION

In all the foregoing discussions and those that follow, reference to particle size is made in specific units of length, i.e. nanometers. These units are to be interpreted in terms of the dimensionless size parameter, $\rho$, by assuming that the incident radiation is in the visible part of the electromagnetic spectrum, i.e. around 500 nm. For this case, a particle of diameter 100 nm would have a $\rho$-value of about 0.6.

Figure 2:
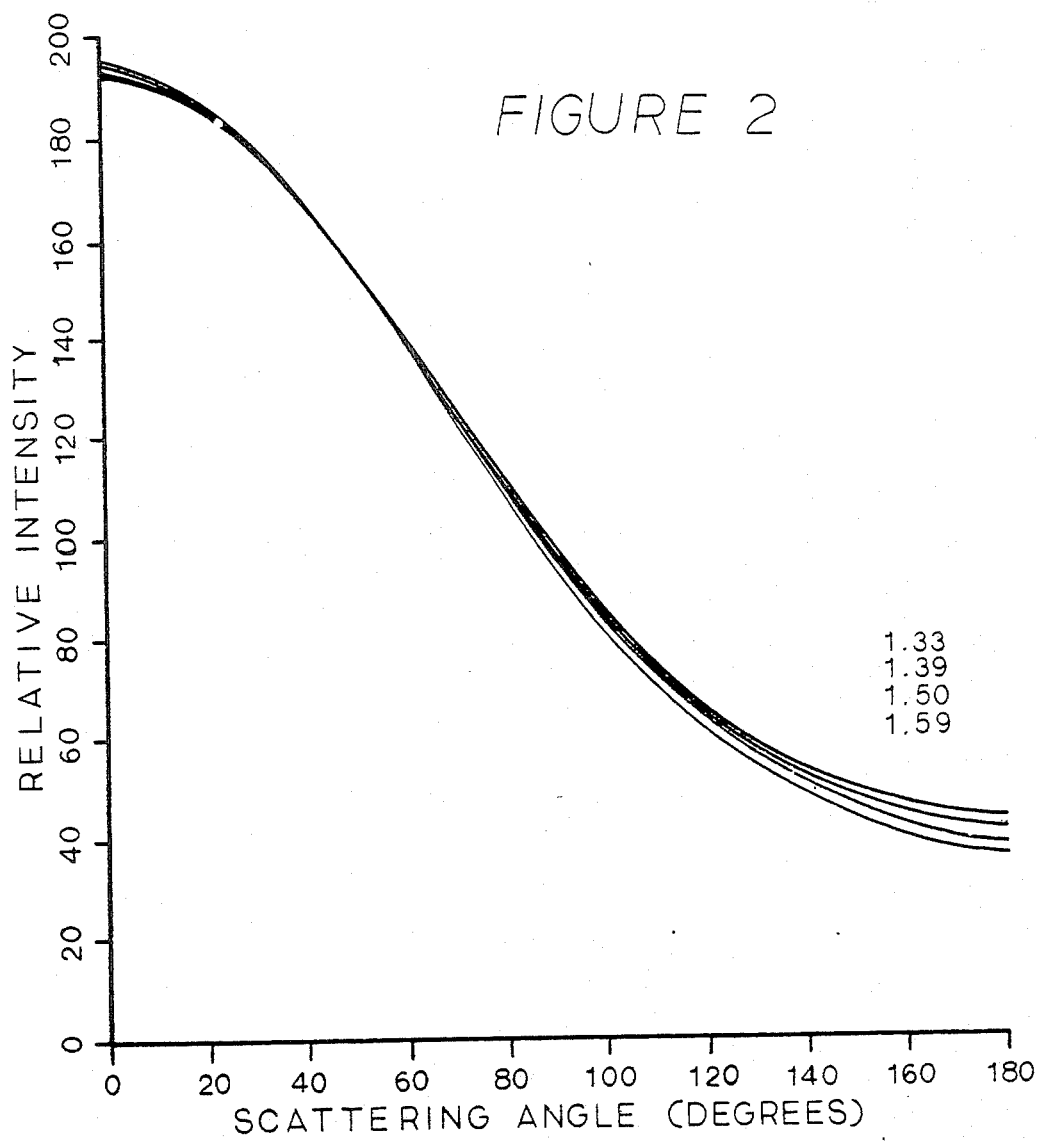
FIG. 2 presents similar data as FIG. 1, but for particles of radius 100 nm.

The accurate characterization and identification of a particle by light scattering means with spatially inhomogeneous light beams requires that particles at least as small as 100 nm by suitably detected and differentiated from their larger particle counterparts. By being able to classify such particles, the associated measuring instrument must be able to cull their larger grazing counterparts, as shall soon be seen. FIG. 1 presents the variation of scattered light intensity with angle for vertically polarized incident light at a wavelength of 514 nm for particles of radius 50 nm and 4 different refractive indices. All curves have been normalized at °. In terms of the strip map identification procedures, the different refractive indices could not be distinguished: only their size could be derived. In examining similar patterns for particles up to about 200 nm, we have confirmed this same type of "degeneracy." FIG. 2, for example, presents a similar plot for particles of radius 100 nm. However, with increasing size (irrespective of refractive index) to this 200 nm limit, we have noted that the forward (20°) to backward (160°) scattered intensity ratio increases to about 5 for the very largest particles in this size range. For these very small particles, the angular resolution of the measurement is not important: we could equally well use the integrated scattered intensities from, say, 20° to 30° divided by the integrated intensities from 150° to 160° and obtain an equivalently monotonic size response for this ratio. Since, furthermore, for the small particles and plane polarized incident light, the azimuthal variation of scattered intensity has a simple $\cos^2 \phi$ form, we can also integrate over all scattering angles $\phi$ and still maintain a monotonic variation of this front/back ratio with size. Naturally, we are talking here about relatively regular small particles whose size and structure have no major effect on the azimuthal scattered intensity.

The reason that we choose to integrate the scattered intensities over such large solid angles is that these smaller particles do not scatter much light: at 100 nm their scattering efficiencies are often only 1%, i.e. the scattering cross section is 1% of the geometrical cross section. By concerning ourselves initially with the problem of detecting and sizing smaller particles, we have discovered a means, to be described presently, to accomplish this while discarding data from larger, grazing particles, which also produce low light level signals.

Figure 3:
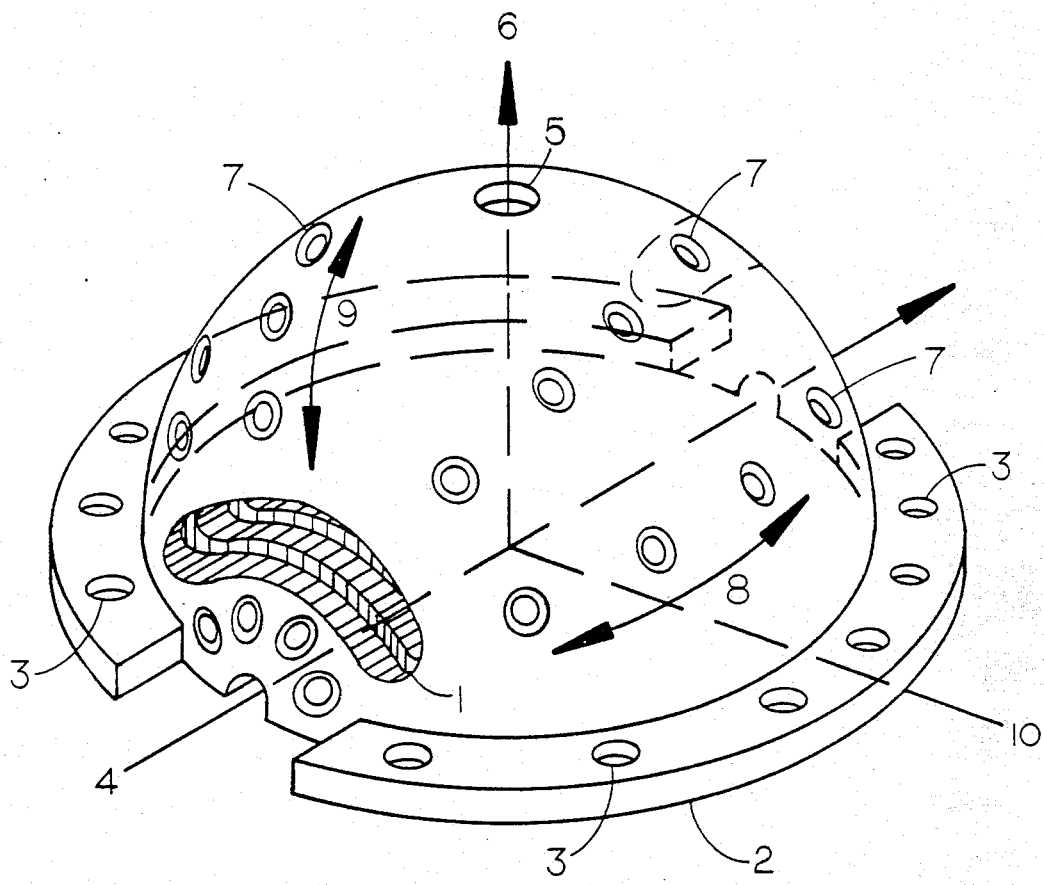
FIG. 3 shows a hemisphere of the apparatus of the preferred embodiment with slots for the special collection means and various ports for other purposes.

The scattering chamber of the preferred embodiment of our invention is a spherical chamber. A hemisphere of this chamber is shown in FIG. 3. It has been designed to collect light from the two large solid angle front-/back regions discussed above. These regions are hereafter called wedge ports or "wedges," i.e. wedges milled out of the sphere in the 20°–30° and 150°–160° direction, respectively. The scattered light passing through these wedge ports is collected subsequently into two corresponding detectors.

FIG. 3 presents a hemispherical section of the preferred embodiment of the invention. The scattering chamber is assembled from two such hemispherical sections attached by means of a flange 2. One hemisphere contains bolt holes 3 in its flange and the opposite hemisphere has threaded holes. Along the Z-axis 4 the light or laser source passes and the aerosol particles are introduced through a port 5 lying on the Y-axis 6. A corresponding port, not shown, on the opposite hemisphere contains an aerosol exhaust port. Between the two hemispheres lies an O-ring to help make the final structure air tight. The flanges lie in the X-Z plane. The X-axis is shown at 10. Also shown in FIG. 3 are sets of small apertures 7 used to hold small photodetectors or optical fibers. In the preferred embodiment of the invention, optical fibers are fused to gradient refractive index lenses, such as the SELFOC lenses manufactured by the Japan Glass Works. These lenses are then inserted into the apertures 7 to provide light collection means at different angular positions on the surface of the sphere with respect to the direction of the incident light beam 4. The other end of the optical fiber is attached to its own distinct photometric detector such as a photomultiplier of the type R647HA manufactured by Hamamatsu Corporation. Alternatively, the fibers from all apertures may be combined and fused to the optical fiber faceplate photocathode of a multianode microchannel plate array tube such as manufactured by the Litton Electron Tube Division of Litton Industries. Light from a given optical fiber would then produce a signal at a single anode of the aforementioned structure. Many other types of optical collection and amplification means will be immediately evident to those of ordinary skill in the art of light scattering measurements and are included here by general reference. Note that in the preferred embodiment of this invention, the various light collecting apertures will be placed along arcs on great circles. If these great circles be spaced at 45° with respect to one another, then the incident light along the Z-axis should be vertically polarized with respect to one of these great circles, say great circle 8. This same beam would then be horizontally polarized with respect to the great circle shown at 90° to it at 9. The two remaining great circles of the preferred embodiment would each lie at 45° with respect to the circles 8 and 9.

Figure 4:
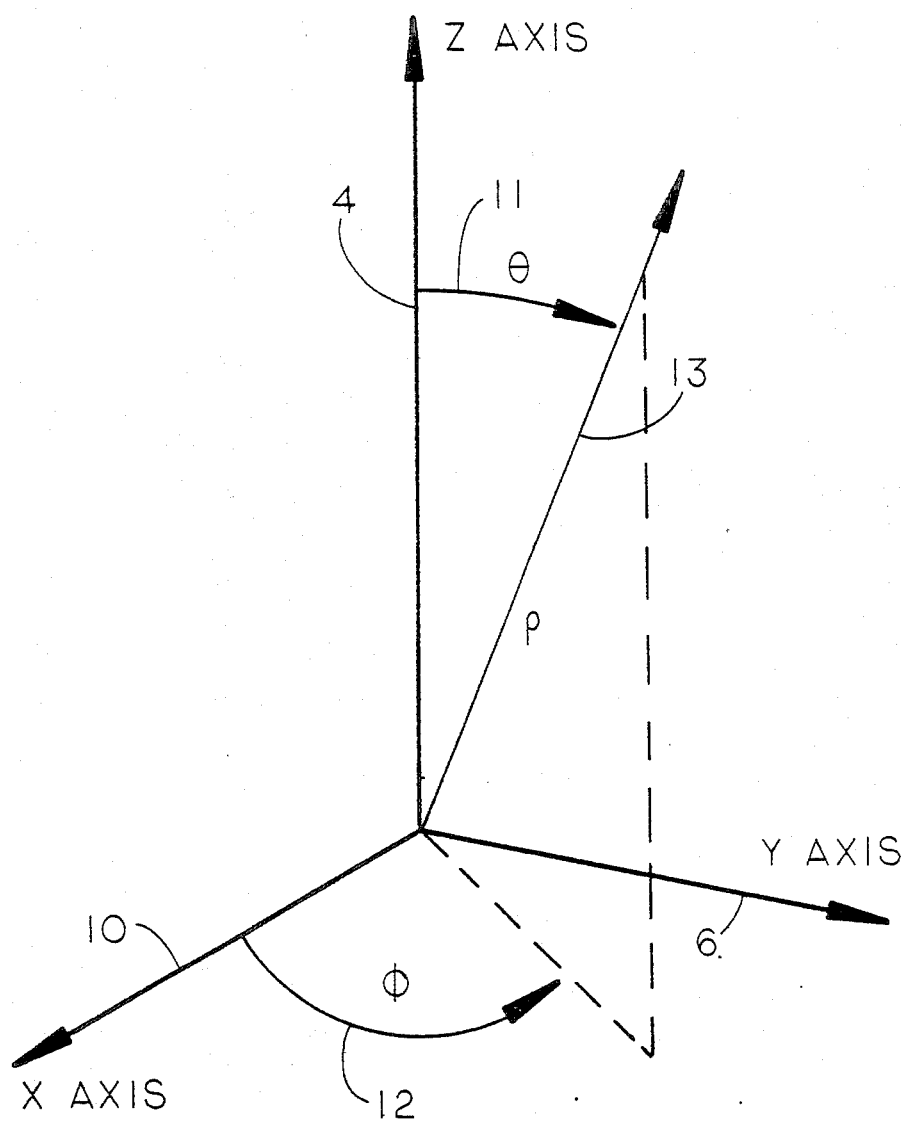
FIG. 4 presents the relationship between Cartesian axes and the polar axes.

FIG. 4 shows the relation between the Cartesian axes 10, 6, and 4 of FIG. 3 and the polar angles $\theta$ at 11 and $\phi$ at 12. The distance to a particular point on the spherical surface is $\rho$ at 13.

Figure 5:
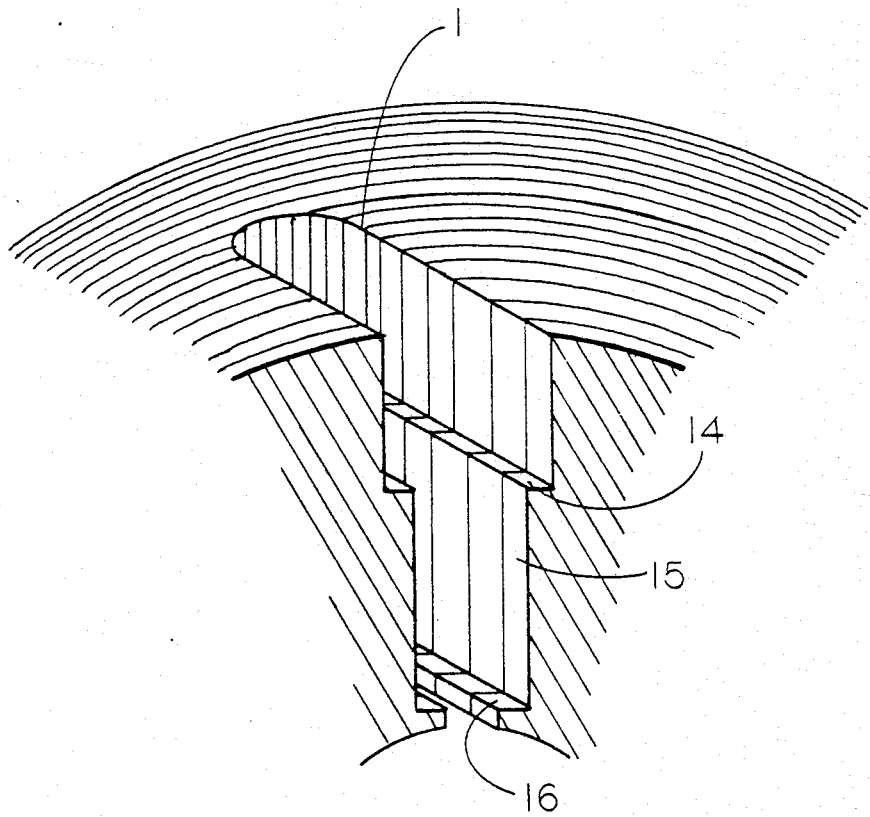
FIG. 5 shows a detail of the port structures of the preferred embodiment.

The special wedge ports, 1, of FIG. 3 are shown in further detail in FIG. 5. They are cut symmetrically into each hemispherical structure. A bundle of optical fibers is fused and placed into each port to depth control means 14. The light incident upon a bundle lying in such a wedge port is further collimated by channel 15 and stop 16.

Figure 6:
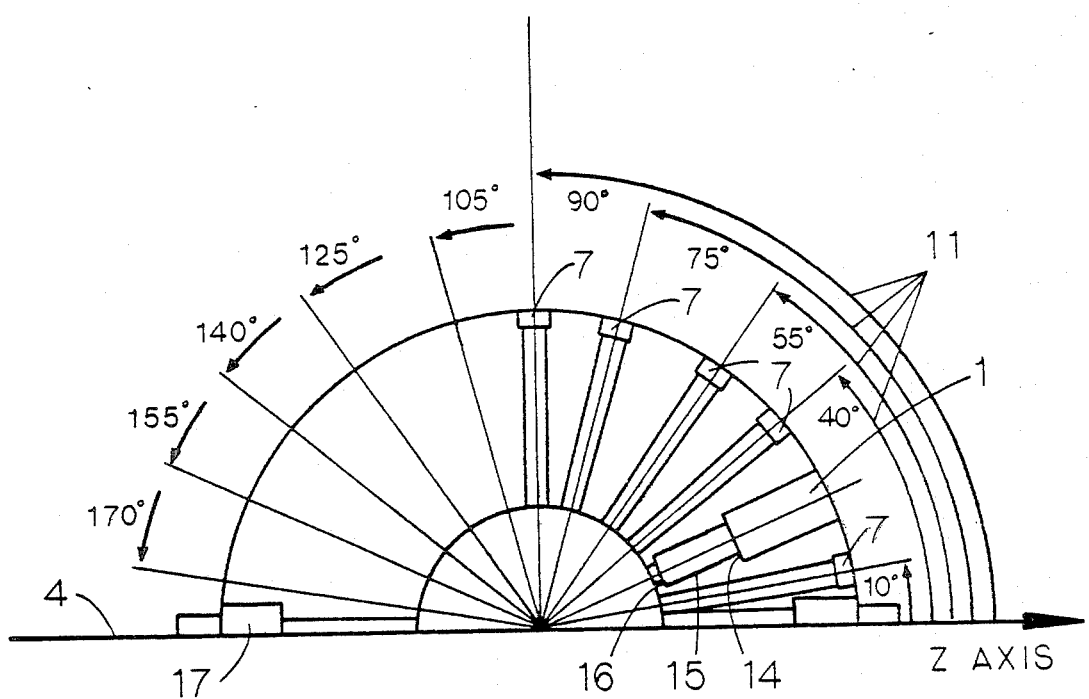
FIG. 6 shows a cross section of a hemisphere through a great circle containing detector means.

FIG. 6 shows a cross sectional view through one of the great circles containing the detector aperture means 7. Details of the apertures of the preferred embodiment are indicated at polar angles 11 from 10° through 90°. Not shown in such detail are the apertures for the angles between 90° and 170°. The wedge port structure for the optical bundles 1 is shown in cross section with bundle stop 14 and collimating elements 15 and 16. The laser or other light source would be attached at 17. Note that the aerosol inlet port 6 of FIG. 3 does not lie in any of the preferred great circles containing detector means 7.

In the preferred embodiment of this invention, the two optical fiber bundles would subtend polar angles 25°±° and 155°±°, front and back respectively. The two forward bundles, one from the top hemisphere and one from the lower hemisphere, would be combined and fused to the photocathode faceplace of a single layer photomultiplier such as the R980 manufactured by Hamamatsu. The two corresponding rear bundles, centered on $\theta = 155°$, would be similarly combined and fused to a separate photomultiplier photocathode.

In the preferred embodiment of this invention, the spherical chamber would have a radius of about 41 mm which would correspond to the optimal collection efficiency of an OPCL-10A SELFOC optical collimator. The diameter of this SELFOC lens is 1.8 mm yielding a solid angle $\Delta \Omega$ subtended at the lens by a scattering particle at the chamber center of about 0.00012 steradian. Each combined optical fiber wedge structure subtends approximately 0.033 steradian. For very small particles scattering flux isotropically, the wedges would collect almost 300 times more scattered flux, making the detection of very small particles practical even for laser sources of modest power. Note that the inner diameter of the chamber of the preferred embodiment is only about 1.5" and the outer diameter is a little over 3". This small size will yield the maximum scattered flux entering each SELFOC lens consistent with its narrow field of view, as has been previously discussed. It also permits the optical fiber bundles to be well collimated and reduces the spurious reflections within the chamber. Finally, this small size results in good air seals and, thereby, helps maintain laminar flow of the aerosol stream.

The means by which data from larger particles that just graze the beam may be recognized and then discarded on the basis of the fiber bundle containing wedge ports 1 is quite straightforward. For all sets of data collected, we must examine the intensity ratio of the front wedge port collected light to the rear wedge port collected light. For the larger particles, this ratio will be very large, often as great as 100:1. If the calculated ratio exceeds, say, 10 then the data would be discarded as long as the front wedge port detector did not approach saturation and most of the individual detector means 7 collected no signals. A larger particle passing through the center of the beam, or near it, will produce a signal that often could saturate the forward wedge port detector. In this event, the data from the other detectors would be kept and processed to characterize the particle by the strip map technique or other means. Naturally, there are various situations whereby the scattered intensity around 25° might be very small for a large, regular or irregular, particle and the resulting ratio not so easy to recognize. We believe that it will be extremely rare to obtain a small ratio without saturating either wedge port detector and thereby misclassify, a large grazing particle as a small particle. A large particle producing an anomalous wedge scattering ratio will also produce signals at most of the remaining detector locations. With a modest illumination source, none of these would detect any signal at all from a very small particle event. Thus, the wedge port scheme will permit the accurate classification of many small particles while preventing the inadvertent misclassification of virtually all larger particles that only graze the beam.

Figure 7:
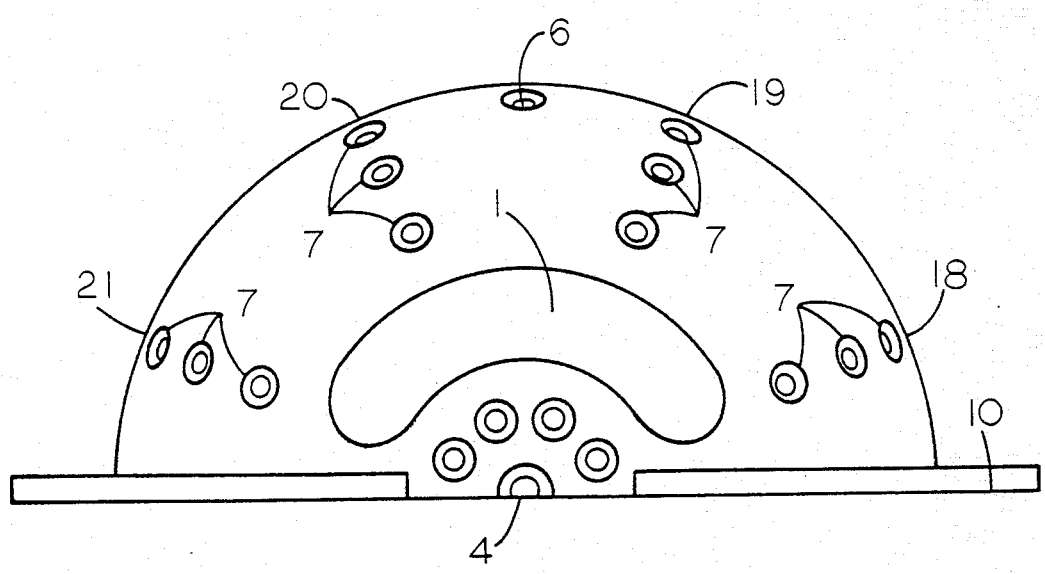
FIG. 7 presents an end view of a single hemisphere.

FIG. 7 shows more details of a scattering chamber hemisphere viewed along the Z-axis. The four detector planes, lying in great circles, are oriented at 22.5°, 67.5°, 112.5° and 157.5° with respect to the X-Y plane, and are shown as 18, 19, 20, and 21, respectively, in FIG. 7. In the preferred embodiment, the electric field of the incident plane polarized laser beam would lie in the 112.5° plane, 20. Thus, the conventional V-plane, is the 22.5° plane 18 and the H-plane lies at 90° to it, i.e. at 112.5°, 20. The two remaining planes, 19 and 21, lie at 45°, respectively, to the V- and H-planes. This geometry of the preferred embodiment permits measurement at all angles, and particularly at 90°, in all planes without obstruction from the aerosol handling system or the flange plane. Also shown in the figure is a typical wedge port 1, various apertures to hold the SELFOC optical collimators 7, the X-axis 10, the Y-axis 6, and the Z-axis 4. The laser enters through the Z-axis 4 and the aerosol through the Y-axis 6.

While there has hereinbefore been presented what is at present considered to be the preferred embodiment or process, it will be apparent to those of ordinary skill in the art that many modifications and variations may be made therefrom without departing from the true spirit and scope of the invention. All such variations and modifications, therefore, are considered to be a part of the invention.

What is claimed is:

1. An instrument for the measurement of the radiation scattered by individual particles comprised of:
   (a) a scattering chamber means of essentially spherical shape containing two diametrically opposed apertures for the insertion and removal respectively, of the particle-containing stream passing through the center of said spherical chamber;
   (b) an incident radiation means providing a collimated beam of radiation passing through said chamber and intersecting said particle-containing stream at the center of said spherical chamber;
   (c) entrance and exit apertures for the passage of the radiation beam through the center of the said chamber means;
   (d) a multiplicity of identical ports at a plurality of angular locations, each subtending a small solid angle with respect to the point of intersection of said aerosol stream and incident radiation beam at the center of said spherical chamber;
   (e) a port subtending a solid angle at least 10 times larger than the solid angle subtended by the ports of (d) and located in the forward direction with respect to the direction of said incident radiation beam;
   (f) a port of structure essentially identical to (e), but located in the backward direction;
   (g) radiation collimation and collection means corresponding and attached to each of the small solid angle ports of (d);
   (h) collimated optical fiber bundles means corresponding and attached to each large solid angle port of (e) and (f), respectively;
   (i) individual detection means corresponding and attached to each collection means of (g) and (h) by which the scattered radiation collected thereby may be converted into an electrical signal.

2. The instrument of claim 1 wherein the incident radiation means is a laser.

3. The instrument of claim 2 where the laser radiation is plane polarized.

4. The instrument of claim 1 wherein the particle-containing stream is a gas.

5. The instrument of claim 1 wherein the multiplicity of small solid angle subtending ports, (g), lie on great circles on said scattering chamber means and said great circles intersect at common points respectively at said radiation entrance and exit aperture means, (c).

6. The instrument of claim 5 wherein said great circles lie at angles 22.5°, 69.5°, 112.5°, and 157.5° with respect to a fixed plane intersecting said spherical chamber and passing through said radiation entrance and exit aperture means, (c).

7. The instrument of claim 1 wherein the scattering chamber means is comprised of two hemispherical sections, said hemispherical sections joining in a plane with said plane passing throguh said radiation entrance and exit apertures and bisecting each.

8. The instrument of claim 7 wherein each hemisphere contains a base flange by which means each may be joined to its corresponding mate.

9. The instrument of claim 1 wherein said larger solid angle subtending ports are comprised of slots centered on angles 25° and 155° with respect to the polar axis defined by the radiation entrance and exit apertures in the direction of the incident radiation beam.

10. The instrumen of claim 1 where the larger solid angle subtending ports subtend polar scattering angles of the order of ±5° with respect to their center.

11. The instrument of claim 10 wherein the larger solid angle subtending ports subtend azimuthal scattering angles up to a maximum of $2\pi$.

12. The instrument of claim 1 wherein the particle-containing stream is a fluid.

13. The instrument of claim 1 wherein the collimation and collection means coresponding and attached to each of said small solid angle ports comprises a collimating means such as a gradient refractive index means centered on and fused to an optical fiber means.

14. The instrument of claim 1 where said detection means are photomultipliers.

15. The instrument of claim 1 where said detection means are photodiodes.

16. A method for characterizing particles with reference to their size parameter $\rho = 2\pi a/\lambda$, where a is the mean particle radius, and $\lambda$ is the wavelength of the incident radiation, comprising the steps of
   (a) entraining the particles in a stream;
   (b) passing said particles sufficiently diluted in said stream through a collimated beam of incident radiation so that at any time essentially only one particle is in said beam;
   (c) collecting the radiation scattered by each said particle into each of a plurality of angular locations by collection means at each said angular location subtending small solid angles with respect to said radiation-scattering particle;

(d) collecting the radiation scattered by each said particle into a forward angular direction by collection means subtending a large solid angle of magnitude at least 100 times greater than the solid angles subtended by the collection means in (c), where forward angular direction refers to a polar scattering angle, $\theta$, less than 90°;

(e) collecting the radiation scattered by each said particle into a backward angular direction by collection means subtending a large solid angle of magnitude at least 100 times greater than the solid angles subtended by the collection means in (c), where backward angular direction refers to a polar scattering angle, $\theta$, greater than 90°;

(f) converting said collected scattered radiation into electrical values by a plurality of detection means, each attached correspondingly to said collection means;

(g) if neither of the electrical signals converted from the large solid angle collections of steps (d) and (e) correspond to saturation of the detection means, then forming the ratio of the electrical value so-converted from radiation collected in step (d) to the electrical value soconverted from radiation collected in step (e);

(h) if the ratio formed in (g) is greater than 5, and if most of the electrical signals converted from the small solid angle collections of step (c) have insignificant associated electrical values, then characterizing the particle size parameter as "large" and performing no further characterizations;

(i) if the ratio formed in step (g) is less than 5 and if most of the small solid angle collections of step (c) have insignificant associated electrical values, then characterizing the particle size parameter as "small" and by reference to said ratio;

(j) if there is a significant electrical value associated with most of the small solid angle collections of step (c), then characterizing the particle by other means.

17. The method of claim 16 where the collimated beam of radiation is visible light from a laser.

18. The method of claim 17 where the light is plane polarized.

19. The method of claim 16 where the radiation collection means are located on the surface of a sphere and the collimated beam of incident radiation lies along a diameter thereof.

20. The method of claim 19 where the plurality of angular locations are on great circles whose common diameter is coincident with the beam of incident radiation.

21. The method of claim 16 where the particle-containing stream is a gas.

22. The method of claim 20 wherein said great circles lie at angles 22.5°, 69.5°, 112.5°, and 157.5° with respect to a fixed plane intersecting said spherical chamber and containing said beam of incident radiation.

23. The method of claim 16 where said collection means are comprised of optical fibers joined to a collimation means.

24. The method of claim 16 where said detection means are photomultipliers.

25. The method of claim 16 where the detection means are photodiodes.

26. The method of claim 23 where the collimation means are gradient refractive index lenses.

27. The method of claim 16 where each collection means subtending a large solid angle includes collection over most azimuthal angles and at least 10° of polar scattering angle.

* * * * *